(12) United States Patent
Strohriegl et al.

(10) Patent No.: US 6,313,326 B1
(45) Date of Patent: Nov. 6, 2001

(54) COMPOUNDS AND THEIR APPLICATION AS WELL AS A METHOD OF PRODUCING LIQUID CRYSTALLINE POLYMERS THEREFROM

(75) Inventors: Peter Strohriegl, Hummeltal; Katja Strelzyk, Ulm; Andreas Stohr, Kriftel; Petra Grundig, Ulm; Michael Gailberger, Neu-Ulm; Fritz Dannenhauer, Hasel; Anne Barth, Neu-Ulm, all of (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/526,756

(22) Filed: Mar. 16, 2000

Related U.S. Application Data

(63) Continuation of application No. 08/953,976, filed on Oct. 20, 1997, now Pat. No. 6,049,000.

(30) Foreign Application Priority Data

Oct. 18, 1996 (DE) .............................................. 196 43 048

(51) Int. Cl.[7] ...................... C07D 303/16; C07D 255/02
(52) U.S. Cl. .............................. 549/561; 549/464; 552/9; 552/10
(58) Field of Search .................................... 549/464, 561; 552/9, 10

(56) References Cited

FOREIGN PATENT DOCUMENTS

| | | |
|---|---|---|
| 44 08 171 A1 | 9/1995 | (DE) . |
| 0 837 054 A2 | 4/1998 | (EP) . |
| WO 95/16007 | 6/1995 | (WO) . |
| WO 97/00600 | 1/1997 | (WO) . |
| WO 97/27252 | 7/1997 | (WO) . |

OTHER PUBLICATIONS

Gangadhara et al., "A New Class of Photo–Cross–Linkable Side Chain Liquid Crystalline Polymers Containing Bis-(benzylidene) cyclohexanone Units," *Macromolecules*, 1995, vol. 28, pp. 806–815.

Römpp–Chemi Lexikon (1990); pp. 1786–1788.

Römpp–Chemi Lexikon (1989); p. 260.

*Primary Examiner*—Richard L. Raymond
(74) *Attorney, Agent, or Firm*—Crowell & Moring LLP

(57) ABSTRACT

The invention relates to compounds with the general formula $Y^1—A^1—M^1—A^2—Y^2$ wherein $Y^1$ and $Y^2$ are different from each other and $Y^1$ is an acrylate or methacrylate residue and $Y^2$ is a vinyl ether, epoxy, or azide residue, $A^1$ and $A^2$ are identical or different residues with the general formula $C_nH_{2n}$ in which n is a whole number from 0 to 20 and one or more methylene groups can be replaced by oxygen atoms, and $M^1$ has the general formula $—R^1—X^1—R^2—X^2—R^3—X^3—R^4—$ wherein $R^1$, $R^2$, $R^3$, and $R^4$ are identical or different doubly bonded residues from the group —O—, —COO—, —CONH—, —CO—, —S—, —C≡C—, —CH=CH—, —CH=N—, —CH$_2$—, —N=N—, and —N=N(O)—, and $R^2—X^2—R^3$ can also be a C—C bond, and $X^1$, $X^2$, and $X^3$ are identical or different residues from the group 1,4-phenylene, 1,4-cyclohexylene; arylalkane or heteroarylalkane with 1 to 10 carbon atoms which contains one to three heteroatoms from the group O, N, and S, substituted with $B^1$, $B^2$, and/or $B^3$; and cycloalkylene with 1 to 10 carbon atoms and substituted with $B^1$, $B^2$, and/or $B^3$, wherein $B^1$, $B^2$, and $B^3$ can be identical or different substituents from the group —H, $C_1$–$C_{20}$-alkyl, $C_1$–$C_{20}$-alkoxy, $C_1$–$C_{20}$-alkylthio, $C_1$–$C_{20}$-alkylcarbonyl, $C_1$–$C_{20}$-alkoxycarbonyl, $C_1$–$C_{20}$-alkylthiocarbonyl, —OH, halogen(fluorine, chlorine, bromine, iodine), —CN, —NO$_2$, cycloalkyl, formyl, acetyl, and alkyl, alkoxy, or alkylthio residues with 1–20 carbon atoms interrupted by ether oxygen, thioether sulfur, or ester groups.

7 Claims, No Drawings

COMPOUNDS AND THEIR APPLICATION AS WELL AS A METHOD OF PRODUCING LIQUID CRYSTALLINE POLYMERS THEREFROM

This application is a continuation of application Ser. No. 08/953,976, filed Oct. 20, 1997 now U.S. Pat. No. 6,049,000.

This application claims the priority of German Application No. 19643048.8-43 filed in Germany on Oct. 18, 1996, the disclosure of which is expressly incorporated by reference herein.

BACKGROUND AND SUMMARY OF THE INVENTION

Polymer coatings and effect paints are extremely important for improvement of surfaces and the esthetic appearance of objects. A wide variety of color impressions and special color effects can be created in many different ways. Current polymer coatings use particles or pigments in a carrier polymer to provide color or achieve special effects such as a metallic sheen or the like. To achieve specific reflection effects, metal flakes, coated mica particles, or interference pigments based on liquid crystalline compounds for example are worked into a clear vehicle as a carrier polymer. Other pigments can additionally be added for free creation of the color impression.

Another possibility for coloration-producing effects consists in the use of liquid crystalline polymers or copolymers, oligomers (macromonomers), or monomers. Some of these liquid crystalline materials are appropriate for forming cohesive polymer films. They polymerize in the liquid crystalline phase and thus produce a paint layer with a special color effect. It is not necessary to work them into a carrier material such as a clear paint.

Known substances that exhibit a liquid crystalline state are generally elongated organic molecules which are able to assume a particular molecular arrangement. Depending on the arrangement of the liquid crystalline phase, only the wavelengths of the incident light that interfere with the equidistant lattice spacing of the liquid crystalline materials are reflected, so that particular color and reflection effects are generated. To make paints and other polymer coatings that exhibit certain wavelength reflections and light effects, it is necessary to fix the liquid crystalline phase or stabilize it mechanically. Particular liquid crystalline phases are formed in certain temperature ranges, whose position and size depends in turn on the chemical structure of the materials. Moreover, the color appearance of the liquid crystalline phases within the phase often depends on temperature, namely as the liquid crystalline phase is heated or cooled, different wavelengths are reflected. To preserve certain color or reflection effects, it is possible to fix a liquid crystalline phase by polymerization or chemical crosslinking of the initial molecules into a dense network. For this purpose, the starting materials must contain crosslinkable reactive groups.

The literature contains liquid crystalline monomer compounds with two identical terminal reactive groups such as diacrylates (J. Lub, D. J. Broer, R. A. M. Hikmet, K. G. J. Nierop, Liquid Crystals 18, 319 (1995)), diepoxides (D. J. Broer, J. Lub, G. N. Mol, Macromolecules 26, 1244 (1993)), and divinyl ethers (R. A. M. Hikmet, J. Lub, J. A. Higgins, Polymer 34, 1736 (1993); S. Jahromi, J. Lub, G. N. Mol, Polymer 35, 622 (1994)). Such monomers are usually crosslinked photochemically by photocycloaddition or by addition of a photoinitiator to the monomer mixture. Likewise, thermally initiated radical crosslinking or thermally initiated addition or condensation reactions are known. With these known monomer compounds, both terminal groups are always polymerized at the same time. To form a polymer film, the known liquid crystalline monomers are applied to the corresponding substrates and the polymerization reaction is initiated, producing the finished end product.

In this process, the application and adhesion of the initial monomers to the coated substrate create considerable difficulties. As a rule, liquid crystalline monomers are crystalline or powdered, so that they adhere poorly to the substrate and are difficult to apply in an even layer. Moreover, the known liquid crystalline materials are relatively invariable in terms of hardness, elasticity, and adhesion of the end product, namely the polymer film, and do not adjust readily to the requirements of specific applications.

The goal of the present invention is to provide compounds and a method of producing liquid crystalline polymers with better handling, processing, and end product properties than the prior art.

This goal is achieved by compounds with general formula $Y^1-A^1-M^1-A^2-Y^2$ wherein $Y^1$ and $Y^2$ are different from each other and $Y^1$ is an acrylate or methacrylate residue and $Y^2$ is a vinyl ether, epoxy, or azide residue, $A^1$ and $A^2$ are identical or different residues with the general formula $C_nH_{2n}$, in which n is a whole number from 0 to 20 and one or more methylene groups can be replaced by oxygen atoms, and $M^1$ has the general formula $-R^1-X^1-R^2-X^2-R^3-X^3-R^4-$ wherein $R^1$, $R^2$, $R^3$, and $R^4$ are identical or different covalently residues from the group $-O-$, $-COO-$, $-CONH-$, $-CO-$, $-S-$, $-C\equiv C-$, $-CH=CH-$, $-CH=N-$, $-CH_2-$, $-N=N-$, and $-N=N(O)-$, and $R^2-X^2-R^3$ or $R^2-X^2-R^3-X^3$ or $X^2-R^3$ can also be a C—C bond, and $X^1$, $X^2$, and $X^3$ are identical or different residues from the group 1,4-phenylene, 1,4-cyclohexylene; arylalkane or heteroarylalkane with 1 to 10 carbon atoms which contains one to three heteroatoms from the group O, N, and S, substituted with $B^1$, $B^2$, and/or $B^3$; and cycloalkylene with 1 to 10 carbon atoms and substituted with $B^1$, $B^2$, and/or $B^3$, wherein $B^1$, $B^2$, and $B^3$ can be identical or different substituents from the group $-H$, $C_1-C_{20}$-alkyl, $C_1-C_{20}$-alkoxy, $C_1-C_{20}$-alkylthio, $C_1-C_{20}$-alkylcarbonyl, $C_1-C_{20}$-alkoxycarbonyl, $C_1-C_{20}$-alkylthiocarbonyl, $-OH$, halogen (fluorine, chlorine, bromine, iodine), $-CN$, $-NO_2$, cycloalkyl, formyl, acetyl, and alkyl, alkoxy, or alkylthio residues with 1–20 carbon atoms interrupted by ether oxygen, thioether sulfur, or ester groups.

At the same time, a method of producing liquid crystalline polymers is provided wherein a) prepolymers are made by polymerization, reacting the acrylate or methacrylate groups $Y^1$ of a compound or a mixture of compounds according to claim 1, and thereafter b) they are crosslinked by polymerization, reacting vinylethyl, epoxy, or azide groups $Y^2$.

The particular advantage of the compounds according to the invention is that, during polymerization, particularly the creation of liquid crystalline polymers, they make a two-step process possible. The compounds proposed have a molecular structure that confers liquid crystalline properties on them. In addition, they have polymerizable residues $Y^1$ and $Y^2$ which make it possible to fix the polycrystalline phase by polymerization. By contrast to known liquid crystalline monomers, which can be used to make liquid crystalline polymer coatings, the various reactive residues $Y^1$ and $Y^2$ of the compounds according to the invention are however crosslinkable by polymerization reactions with various initiation and reaction mechanisms. By polymerization of acrylate or methacrylate groups $Y^1$, prepolymers can be made with degrees of polymerization that are not too high (oligomers). These oligomers form glasses, but still do not have sufficiently low viscosity to ensure good orientation. Moreover, by the usual methods of polymer chemistry, the molecular weight and other material parameters such as viscosity, film-forming properties, leveling, flow properties, solubility, color, sheen, swelling, workability, adhesion, elasticity, hardness, etc. can be affected.

A particularly advantageous property of the reactive groups $Y^1$ and $Y^2$ of the compounds according to the invention is that the initiation and reaction of prepolymerization of reactive groups $Y^1$ can take place without the reactive groups $Y^2$ being reacted. The resultant oligomers can be readily further processed following prepolymerization and have outstanding application properties by comparison to the known polycrystal monomers. The viscosity of the prepolymers makes it possible for example to apply them before final crosslinking like a paint with good leveling properties, good flow properties, high sprayability, and outstanding adhesion to the substrate to be coated. In a further polymerization step, the vinyl ether, epoxy, or azide groups $Y^2$ that are still free are crosslinked. Adhesion of the end product to the substrate can be adjusted, for example by concentrating the reactive groups $Y^2$, to the substrate in question.

The compounds according to the invention have still further advantages. Polymerization of the liquid crystalline materials is preferably done in two steps with prepolymerization. They can also be polymerized directly on a substrate with both functional groups $Y^1$ and $Y^2$ being polymerized. The user is thus able to choose between a one-step and a two-step polymerization process or combine them according to the application.

Particularly advantageous liquid crystalline monomers are compounds in which $Y^1$ is an acrylate group and $Y^2$ is a vinyl ether group. It is also advantageous for the number n of carbon atoms of residues $A^1$ and $A^2$ to be 1 to 10, and particularly preferably 2 to 6. It is advantageous for the liquid crystalline properties for the residues $R^1$, $R^2$, $R^3$, and/or $R^4$ to be —O—, —COO—. It is also advantageous for the $X^1$ and $X^3$ residues to be 1,4-phenylene and/or for $R^2$—$X^2$—$R^3$ to be a C—C bond.

In a preferred embodiment of the method for producing liquid crystalline polymers, polymerization (a) is carried out by reacting the acrylate or methacrylate groups $Y^1$ radically and polymerization (b) by reacting the vinyl ether, epoxy, or azide groups $Y^2$ preferably photochemically, and particularly preferably cationically. Since polymerization reaction (a) is usually inhibited by oxygen, it is advantageous to conduct it in an organic solvent, preferably in degassed, absolute tetrahydrofuran. It is appropriate to initiate this reaction and to continue it, in the presence of a radical polymerization initiator, preferably 2,2'-azobis-(2-methylpropionitrile), dibenzoyl peroxide, or di-t-butyl peroxide, particularly preferably with an initiator concentration of 1 to 5 mol. %. For polymerization reaction (a), it is advantageous for there to be a reaction regulator, preferably 1-decanethiol, particularly preferably with a reaction regulator concentration of 1 to 10 mol %.

The various initiation and reaction mechanisms of radical polymerization of acrylate or methacrylate groups $Y^1$ to the prepolymer on the one hand and the photochemical cationic polymerization (b) of vinyl ether, epoxy, or azide groups $Y^2$ to the end product on the other hand, ensure that in the first step, when residue $Y^1$ is being crosslinked, no reaction takes place with residues $Y^2$ or of residues $Y^2$ with one another. Since cationic polymerization by contrast with radical polymerization is not inhibited by oxygen, this makes the process simpler and simplifies handling of the prepolymer during crosslinking on the substrate. No steps need be taken to exclude oxygen by expensive inert gas technologies.

When prepolymerization (a) is conducted in an organic solvent, the oligomers, which are easy to handle, can be made in large quantities regardless of where they are further converted to the end product. The prepolymers usually have a very long shelf life.

By using a radical polymerization initiator and possibly adding a reaction regulator, the reaction conditions can be optimized in terms of yield and product properties.

For many applications, it is particularly advantageous to isolate the prepolymer after polymerization reaction (a). For this purpose, it is advantageous to precipitate it from hexane after polymerization reaction (a) and then advantageously reprecipitate and/or dry it.

For the application, to be able to apply the prepolymer like a paint to the substrate to be coated, it is particularly advantageous to dissolve it before polymerization (b) of the vinyl ether, epoxy, or azide groups in an organic solvent, preferably in chloroform or tetrahydrofuran, and to evaporate the solvent before the reaction itself.

The form of the prepolymer to be applied can be adapted to a great variety of application requirements. For example, it can also be sold in the solvent instead of the monomeric compounds, so that the end user need not make the prepolymer, saving work steps, manufacturing facilities, and cost. Moreover, solutions of the prepolymer can be made in any concentration and with specific viscosity, flow, wetting, and adhesion properties. Application to the substrate to be coated can be done in any suitable manner. Thus, for example, surfaces can be sprayed or painted or dipped in the solution of prepolymer. Depending on the requirement and the solvent used, it can be evaporated at room temperature or at an elevated temperature, at a negative pressure, or in an air stream. It must be borne in mind in this connection that polymerization reaction (b) with certain compositions already begins at an elevated temperature, which may be advantageous for certain applications.

In a preferred embodiment of the invention, polymerization (b) is conducted by reacting the vinyl ether, epoxy, or azide group in the presence of at least one photoinitiator, preferably a cationic photoinitiator. Advantageously the photoinitiator is present in a quantity of 0.5 to 10 wt. %, preferably 1 to 5 wt. %, and/or contains a diarylsulfonium salt, a diaryliodonium salt, or a mixture thereof. Examples of such photoinitiators are the commercial products Degacure KI 85 (Degussa), bis(4-tert-butylphenyl)iodonium hexafluorophosphate (Midori Chemical), 2,4,6-trimethylbenzoylethoxyphenylphosphine oxide (BASF) mixed with diphenyliodonium hexafluorophosphate, and 2,2-dimethoxy-2-phenylacetophenone mixed with diphenyliodonium tetrafluoroborate. Normally, polymerization reaction (b) is induced by ultraviolet radiation and/or the reaction product is post-cured by heat treatment.

The use of a photoinitiator has particular advantages since the course of the reaction up to the end product can be more easily initiated, regulated, and accelerated. By comparison to purely thermal curing of the prepolymers, induction of the polymerization reaction by ultraviolet radiation saves considerable energy cost, and is faster and more readily initiated, and easier to quantify. Heat treatment has advantages if the surface to be coated cannot be reached by the initiation radiation because it is in the shadow or inaccessible.

In a particularly preferred embodiment of the method of the present invention, polymerization (a) is conducted in the presence of additional compounds with the general formula $Y^3-A^3-M^2-A^4-Y^4$ or $(Y^3-A^3)_2-M^2-A^4Y^4$ wherein $Y^3$ can be an acrylate or methacrylate group and $Y^4$ can be a polymerizable residue from the group of vinyl ether, epoxy, and azide residues or a nonpolymerizable residue from the group —H, —CN, and cholesteryl, $A^3$ and $A^4$ are identical or different residues with the general formula $C_nH_{2n}$ in which n is a whole number from 0 to 20 and one or more methylene groups can be replaced by oxygen atoms, and $M^2$ has the general formula $-R^5-X^4-R^6-X^5-R^7-X^6-R^8-$ wherein $R^5, R^6, R^7$ and $R^8$ are identical or different doubly bonded residues from the group —O—, —COO—, —CONH—, —S—, —C≡C—, —CH=CH—, —CH=N—, —CH$_2$—, —N=N—, and —N=N(O)—, and $R^6-X^5-R^7$ or $R^6-X^5-R^7-X^6$ can also be a C—C bond and $X^4, X^5,$ and $X^6$ are identical or different residues from the group 1,4-phenylene, 1,4-cyclohexylene; arylalkane or heteroarylalkane with 1 to 10 carbon atoms which contains one to three heteroatoms from the group O, N, and S, substituted with $B^1, B^2,$ and/or $B^3$; and cycloalkylene with 1 to 10 carbon atoms and substituted with $B^1, B^2,$ and/or $B^3$, wherein $B^1, B^2,$ and $B^3$ can be identical or different substituents from the group —H, $C_1-C_{20}$-alkyl, $C_1-C_{20}$-alkoxy, $C_1-C_{20}$-alkylthio, $C_1-C_{20}$-alkylcarbonyl, $C_1-C_{20}$-alkoxycarbonyl, $C_1-C_{20}$-alkylthiocarbonyl, —OH, halogen (fluorine, chlorine, bromine, iodine), —CN, —NO$_2$ cycloalkyl, formyl, acetyl, and alkyl, alkoxy, or alkylthio residues with 1–20 carbon atoms interrupted by ether oxygen, thioether sulfur, or ester groups.

These additional compounds, hereinafter known as comonomers, are particularly suitable for matching the properties of the polymerization end product to the application requirements in question. The adjustable mechanical properties of the end product are in particular adhesion, elasticity, and hardness of the polymer film on the substrate in question.

The use according to the invention of the comonomers to control the optical effect of the polymer film is particularly advantageous. Here it is particularly advantageous for residues $A^3$ and/or $A^4$ to be chiral. By using one or more chiral or chiral-nematic comonomers in different ratios mixed with the monomers of the present invention, any reflection wavelengths of the polymer films, from the ultraviolet to the infrared range, can be established. By copolymerization with the chiral compounds, highly crosslinked polymer films result, in which the reflection wavelength does not depend on temperature. Because of the chirality of the compounds, cholesteric side group prepolymers are formed in polymerization (a) which are then fixed as a cholesteric network in polymerization reaction (b).

Examples of comonomers suitable according to the invention are the following compounds:

4-[(S)-(2-acryloyloxy-2-methyl)ethoxy]-4'-cyanobiphenyl

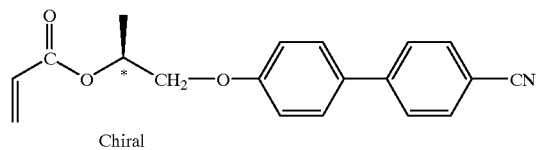

Chiral

4-[(S) -2-acryloyloxy-2-methyl)ethoxy]-4'-[(S)-2-methylbutoxyl]-biphenyl

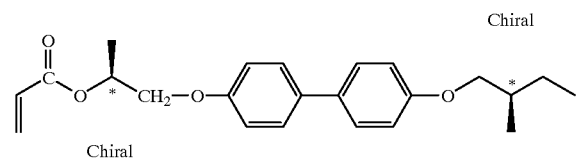

Chiral

{4'-[(S)-(2-acryloyloxy-2-methyl)ethoxy]phenyl}4-(2-vinyloxyethoxy)benzoate

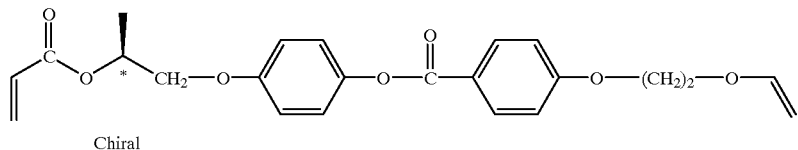

Chiral

Preferably, the copolymers have only one or two polymerizable residues $Y^3$, which are exclusively involved in first polymerization reaction (a). Copolymers with only one acrylate or methacrylate group affect not only the optical effect but also the mechanical properties of the prepolymer and the end product. Such copolymers lead to chain terminations in the polymerization reaction and thus regulate the degree of crosslinking. The chiral centers $A^3$ and/or $A^4$ of the comonomers favor formation of a cholesteric phase in the liquid crystalline polymer. Such a cholesteric structure, which can only be accomplished with optically active molecules and represents a type of superstructure on the liquid crystalline textures of simple structure, contains liquid crystalline unit regions in a screw-shaped helical arrangement. The height of the individual helical unit regions, also known as pitch, determines the wavelength of the reflected light and hence the colors of the metallically iridescent reflections of the polymer film.

Examples of chiral vinyl ethers and divinyl ethers, suitable according to the invention as comonomers with free vinyl ether groups, and favoring a cholesteric phase, are the following compounds:

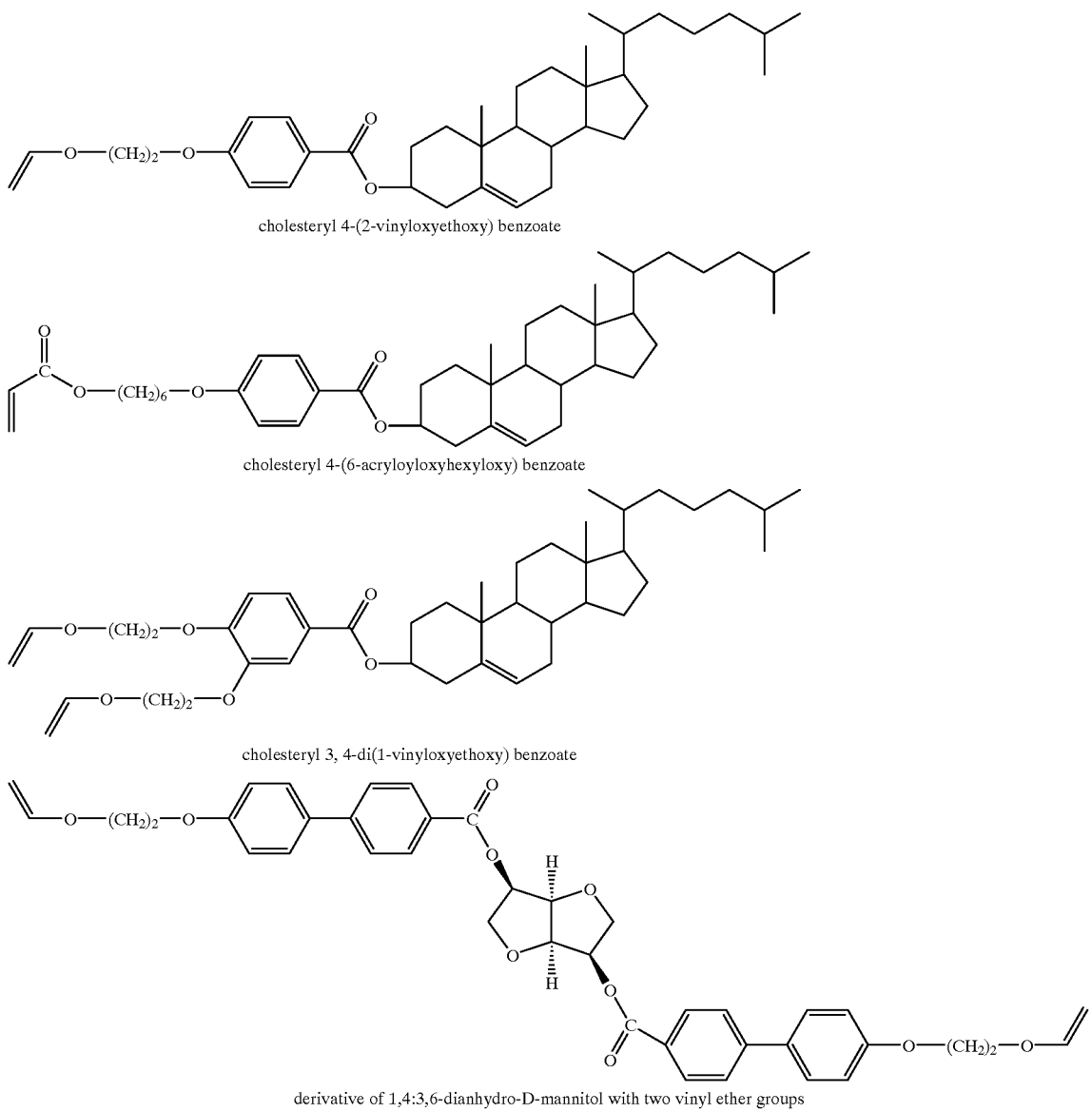

cholesteryl 4-(2-vinyloxyethoxy) benzoate cholesteryl 4-(6-acryloyloxyhexyloxy) benzoate cholesteryl 3, 4-di(1-vinyloxyethoxy) benzoate derivative of 1,4:3,6-dianhydro-D-mannitol with two vinyl ether groups Further advantages, features, and applications of the present invention will become clear from the preferred embodiments hereinbelow.

EXAMPLE 1

A) 4-(2-Vinyloxyethoxy)benzoic acid 4'-(6-acryloyloxy-hexyloxy)phenyl ester

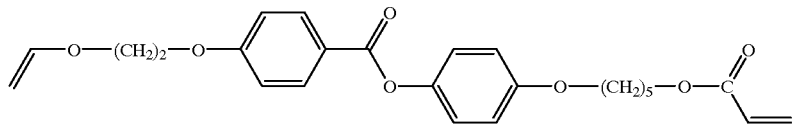

4.37 g (0.021 mole) of 4-(2-vinyloxyethoxyl)benzoic acid is dissolved in 80 mL of 1,2-dimethoxyethane and 4.25 g (0.042 mole) of triethylamine was added. At −30° C., 2.41 g (0.021 mole) methanesulfonyl chloride was added dropwise to the solution such that the temperature did not go above −25° C. After one hour agitation at −30° C., 5.56 g (0.021 mole) 4-(6-acryloyloxyhexyloxy)phenol, 0.024 g (0.002 mole) 4-dimethylaminopyridine, and 100 mg 2,6-di-tert-butyl-p-cresol was added to the reaction solution and agitated for a further three hours at 0 to 5° C. The resulting precipitate was then filtered off and the filtrate was evaporated under vacuum in a rotary evaporator. The residue was recrystallized from 80 mL isopropanol. The product is obtained with a yield of 78% (7.42 g).

B) Synthesis of Precursors a) 4-(2-Vinyloxyethoxy)benzoic acid

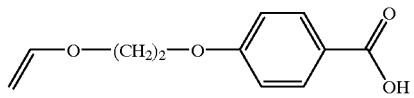

11.3 g (0.069 mole) ethyl 4-hydroxybenzoate was dissolved in 200 mL cyclohexanone in an inert atmosphere. After addition of 18.8 g (0.136 mole) potassium carbonate, 1.0 g potassium iodide, and 8.0 g (0.075 mole) 2-chlorethyl vinyl ether, the reaction mixture was refluxed for five hours. The solid was then filtered off and rinsed with a little cyclohexanone.

When the cyclohexanone was drawn off under vacuum, the residue was taken up in 300 mL methanol and a solution of 19.04 g (0.43 mole) KOH in 50 mL water was added. The reaction mixture was then refluxed for 17 hours. The solvent was then drawn off in a vacuum and the residue was added to 300 mL 0.5 M aqueous NaOH. After washing three times with 80-mL portions of diethyl ether, the aqueous phase was acidified with conc. HCl, the resultant precipitate was filtered off, and recrystallized after drying, from 100 mL toluene. The yield was 9.49 g (67%.)

b) Synthesis of 4-(6-acryoyloxyhexyloxy)phenol

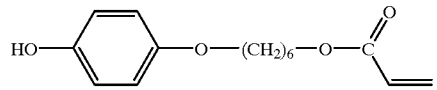

is done according to R. A. M. Hikmet, J. Lub, A. J. W. Tol, Macromolecules 28, 3313 (1995).

EXAMPLE 2

4-[(S)-(2-Acryloyloxy-2-methyl)ethoxy]-4'-cyanobiphenyl

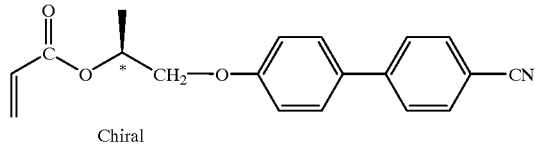

The compound wssynthesized similarly to the corresponding methacrylate as described in J. M. G. Cowie, H. W. Hunter, Makromol. Chem. 191, 1339 (1990).

EXAMPLE 3

Synthesis of an Oligoacrylate With Free Vinyl Ether Groups 1.0 g of monomer 1 was dissolved in 10 mL absolute THF. 2 mol % 2,2'-azobis(2-methylpropionitrile) as the initiator and 4 mol % 1-decanethiol as the regulator were added to the solution. After degassing three times, it was polymerized while stirring for 48 hours at 60° C.

The solution was then precipitated from 400 mL hexane, the polymer was dissolved in 8 mL CHCl$_3$ and reprecipitated from 400 mL methanol. After drying in a vacuum oven at 50° C. overnight, the yield was 85%.

Characterization

The polymer had a nematic phase with a clear point at approximately 100° C. In $^1$H NMR the vinyl ether bands are still detectable at 6.5 ppm and 4.2 ppm. After GPC, M$_n$~20,000.

EXAMPLE 4

Synthesis of Cholesteric Cooligoacrylates With Free Vinyl Ether Groups 1.0 g of a mixture of monomers 1 and 2 was dissolved in 10 mL absolute THF. 2 mol % 2,2'-azobis(2-methylpropionitrile) was added as the initiator and 4 mol % 1decanethiol was added as the regulator. After degassing three times, it was polymerized for 48 hours at 60° C. wile stirring.

The solution was then precipitated from 400 mL hexane, the polymer was dissolved in 8 mL CHCl$_3$, and reprecipitated from 400 mL methanol. It was then dried overnight in a vacuum oven at 50° C.

A cooligoacrylate was obtained with vinyl ether groups that are still free. The polymer can then be crosslinked cationically with these.

EXAMPLE 5

Cationic Photocrosslinking of Films of the Cooligoacrylates

The prepolymerized cholesteric cooligoacrylate with free vinyl ether groups was dissolved in CHCl$_3$ or THF. After addition of 1 to 5 wt. % cationic photoinitiator Dagacure KI 85 (Degussa), the solution was spread over a substrate and the solvent was evaporated off. The prepolymer layer was then crosslinked cationically in the cholesteric phase by irradiation with UV light. After irradiation, the film was completely insoluble and its texture will no longer change. Depending on the ratio of monomers 1 and 2, the reflection wavelength of the polymer layer was in the visible spectral range, so that the film is colored and has a metallic sheen.

EXAMPLE 6

4-[(S)-(2-Acryloyloxy-2-methyl)ethoxy]-4'-[(S)-2-methylbutoxy]biphenyl

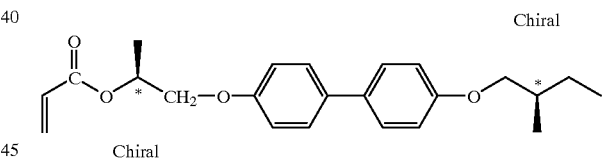

The chiral precursor 4-hydroxy-[4'-2-methyl]butoxy] biphenyl of monomer 3 was synthesized according to R. Zentel, G. Reckert, B. Reck, Liquid Crystals 2, 83 (1987). Further synthesis of monomer 3 was done similarly to synthesis of monomer 2.

EXAMPLE 7

Synthesis of Cholesteric Cooligoacrylates With Free Vinyl Ether Groups 1.0 g of a mixture of monomers 1 and 3 was dissolved in 10 mL of absolute THF. 2 mol % 2,2'-azobis(2-methylpropionitrile) was added to the solution as the initiator and 4 mol % 1-decanethiol was added as the regulator. After degassing three times, it wss polymerized for 48 hours at 60° C. while stirring.

The solution was then precipitated from 400 mL hexane, the polymer was dissolved in 8 mL CHCl$_3$, and reprecipitated in 400 mL methanol. It was then dried overnight in a vacuum oven at 50° C.

A cooligoacrylate was obtained with vinyl ether groups that are still free. The polymer was then crosslinked cationically with these groups.

EXAMPLE 8

Cationic Photocrosslinking of Films of Cooligoacrylates

The prepolymerized cholesteric cooligoacrylate with free vinyl ether groups was dissolved in $CHCl_3$ or THF. After addition of 1 to 5 wt. % cationic photoinitiator Dagacure KI 85 (Degussa), the solution was spread over a substrate and the solvent was evaporated off. The prepolymer layer was then crosslinked cationically in the cholesteric phase by irradiation with UV light. After irradiation, the film was completely insoluble and its texture will no longer change. Depending on the mixing ratio of monomers 1 and 3, the reflection wavelength of the polymer layer is in the visible spectral range, so that the film is colored and has a metallic sheen.

EXAMPLE 9

A) Cholesteryl 4-(6-acryloyloxyhexyloxy)benzoate

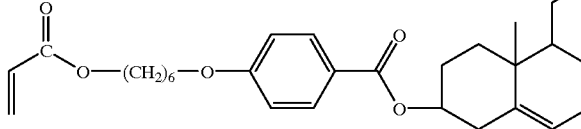

2.92 g (0.01 mole) 4-(6-acryloyloxyhexyloxy)benzoic acid is dissolved in 10 mL $CHCl_3$ and two drops of N,N-dimethylformamide and 30 mg of 2,6-di-tert-butyl-p-cresol were added. Next, 15 mL thionyl chloride was added dropwise to the solution which was stirred at 70° C. until no more gas was given off (approx. 1–2 hours). Then, the $CHCl_3$ and excess thionyl chloride were distilled off under vacuum. The residue is 4-(6-acryloyloxyhexyloxy)benzoyl chloride.

The acid chloride was dissolved in 30 mL absolute ether and at 0 to 50° C. added dropwise to 3.86 g (0.01 mole) cholesterol in 10 mL pyridine. It was then stirred for 17 hours at 50° C.

For workup, the solution was poured into 200 to 300 mL ice water and acidified with conc. HCl. The product precipitated as a white precipitate. The precipitate was filtered off, washed with saturated $NaHCO_3$ solution, and then with $H_2O$. It was then recrystallized twice from 100-mL portions of ethanol. After drying, 4.5 g (69%) white crystals 27 are obtained.

Characterization $^1$H NMR ($CHCl_3$): 0.65 (s, 3H); 0.8 to 2.1 (m, 46 H); 2.45 (m, 2H); 3.88 (t, 2H); 4.15 (t, 2H); 4.821 (m, 1H); 5.40 (m, 1H); 5.80 (dd, 1H); 6.10 (dd, 1H); 6.38 (dd, 1H); 6.85 (d, 2H); 7.95 (d, 2H) ppm $^{13}$C NMR ($CDCl_3$): 11.82; 18.68; 19.34; 21.01; 22.52; 22.78; 23.80; 24.24; 25.66; 27.95; 28.19; 28.49; 28.96; 31.85; 35.75; 36.15; 36.60; 37.01; 38.25; 39.47; 39.70; 42.47; 50.00; 56.10; 56.64; 64.39; 67.87; 74.12; 113.89; 122.59; 123.05; 128.52; 130.44; 131.46; 139.71; 162.66; 165.69; 166.20 ppm IR (KBr): 2943; 2866; 1717; 1634; 1605; 1510; 1273; 1250; 1198; 1167; 1115; 1007; 772 cm$^{-1}$ Phase properties $^{a)}$: k97 s 161 ch 200 i
$^{a)}$Polarizing Microscope Heating rate 10 Kmin$^{-1}$; second heating; 1 wt. % 4-methoxyphenol as inhibitor. No DSC data are obtainable since the compound completely polymerizes. Under the polarizing microscope, the phase transitions can be observed at the edges of the samples.

B) Synthesis of Precursors a) ethyl 4-(6-hydroxyhexyloxy)benzoate 16.6 g (0.1 mole) ethyl 4-hydroxybenzoate is added to a solution of 4.0 g (0.12 mole) NaOH in 300 mL 2-butanone. After addition of 15.0 g (0.1 mole) NaI and 16.01 mL (0.12 mole) 6-chlorohexanol the mixture was stirred for 10 hours at 60° C.

The solvent was distilled off under water aspirator vacuum (WV), the residue was washed with 300 mL 0.4 M NaOH, and extracted four times with 80-mL portions of ether. The ether phases were combined, dried over $Na_2SO_4$, then the ether was evaporated in a rotary evaporator under water aspirator vacuum.

The residue was a yellow solid 4-(6-hydroxyhexyloxy) benzoic acid ethyl ester which is used without further purification.

Yield: 23.5 g (88%).

b) 4-(6-Hydroxyhexyloxy)benzoic acid 23.5 g (0.088 mole) ethyl 4-(6-hydroxyhexyloxy) benzoate (as crude product) was added to 300 mL 0.5 M KOH and refluxed for 5 hours.

The solution was then washed three times with 80-mL portions of ether and the aqueous phase was acidified with HCl. The precipitated product was filtered off, washed in $H_2O$, and recrystallized from 250 mL ethanol.

After drying under vacuum, 9.7 g (50%) white crystals were obtained.

Characterization $^1$H NMR (THF-dg): 1.65 (m, 6H); 1.95 (m, 2H); 3.65 (t, 2H); 4.20 (t, 2H); 7.10 (d, 2H); 8.10 (d, 2H) ppm IR(KBr): 3404; 2947; 2911; 1690; 1605 cm$^{-1}$ c) 4-(6-Acryloyloxyhexyloxy)benzoic acid 16.0 g (0.067 mole) 4-(6-hydroxyhexyloxy)benzoic acid is added to a solution of 9.34 mL (0.074 mole) N,N-dimethylaniline in 90 mL 1,4-dioxane.

At 60° C., 6.01 mL (0.074 mole) of freshly distilled acryloyl chloride was added slowly dropwise. It was then stirred for 2 hours at 60° C. When water was added, the product precipitated as a white precipitate and was then filtered off.

For purification, the product was recrystallized in 200 mL 2-propanol. After drying 14.6 g (75) of white crystals were obtained.

Characterization $^1$H NMR ($CDCl_3$): 1.45 (m, 4H); 1.70 (M, 2H); 1.80 (m, 2H); 4.00 (t, 2H); 4.15 (t, 2H); 5.80 (dd, 1H); 6.10 (dd, 1H); 6.38 (dd, 1H); 6.90 (d, 2H); 8.05 (d, 2H) ppm IR(KBr): 2940; 1730; 1688; 1607; 1431; 1410; 1315; 1296; 1198; 1169; 986; 770 cm$^{-1}$ Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A compounds having the formula, $Y^1—A^1—M^1A^2—Y^2$ wherein $Y^1$ and $Y^2$ are different from each other and $Y^1$ is an acrylate or methacrylate residue and $Y^2$ is an epoxy or azide residue, $A^1$ and $A^2$ are identical or different residues with the general formula $C_nH_{2n}$ in which n is a whole number from 0 to 20 and one or more methylene groups can be replaced by oxygen atoms, and $M^1$ has the general formula $—R^1—X^1—R^2—X^2—R^3—X^3—R^4$ wherein $R^1$, $R^2$, $R^3$, and $R^4$ are identical or different doubly bonded residues selected from the group consisting of $—O—$, $—C(O)O—$, $—O(C)O—$, $—CONH—$, $—CO—$, $—S—$, $—C\equiv C—$, $—CH=CH—$, $—CH=N—$, $—CH_2—$, $—N=N—$, $—N=N(O)—$, and $R^2—X^2—R^3$ or $R^2—X^2—R^3—X^3$ or $X^2—R^3$ can also be a C—C bond, whereby n in $A^1$ or $A^2$ is a whole number from 1 to 20 when $R^1$ or $R^4$ is $—O—$, and $X^1$, $X^2$, and $X^3$ are identical or different heteroarylkylene residues having 6 to 10 carbon atoms and having one to three hetereoatoms selected from the group consisting of O, N, and S, and cycloalkylene having 3 to 10 carbon atoms and, wherein $X^1$, $X^2$, and $X^3$ are substituted with at least one of $B^1$, $B^2$, and $B^3$ wherein $B^1$, $B^2$, and $B^3$ can be identical or different substituents selected from the group consisting of —H, $C_1-C_{20}$-alkyl, $C_1-C_{20}$-alkoxy, $C_1-C_{20}$-alkylthio, $C_1-C_{20}$alkylcarbonyl, $C_1-C_{20}$-alkoxycarbonyl, $C_1-C_{20}$-alkylthiocarbonyl, —OH, a halogen, —CN, —NO$_2$, cycloalkyl, formyl, and alkyl, alkoxy, or alkylthio residues with 1 to 20 carbon atoms interrupted by ether oxygen, thioether sulfur or ester groups.

2. A compound according to claim 1, wherein $Y^1$ is an acrylate.

3. A compound according to claim 1, wherein n is a whole number from 1 to 10.

4. A compound according to one of claim 1, wherein at least one of $R^1$, $R^2$, $R^3$, or $R^4$ are selected from the group consisting of —O—and —COO—.

5. A compound according to claim 1, wherein $R^2—X^2—R^3$ is a C—C bond.

6. The compound according to claim 1, wherein a halogen further comprises at least one of the members selected from the group consisting of fluorine, chlorine, bromine and iodine.

7. A compound according to claim 3, wherein n is a whole number between 2 and 6.

* * * * *